United States Patent [19]

Panasik et al.

[11] 4,066,457
[45] Jan. 3, 1978

[54] COLOR DEVELOPER FOR DIFFUSION TRANSFER

[75] Inventors: Theodore Panasik, Vestal; Felix Viro, Apalachin; Burton H. Waxman, Endwell; Robert T. Shannahan, Endicott, all of N.Y.

[73] Assignee: GAF Corporation, New York, N.Y.

[21] Appl. No.: 531,400

[22] Filed: Dec. 10, 1974

[51] Int. Cl.² ............ G03C 7/00; G03C 5/54; G03C 5/30; G03C 1/40
[52] U.S. Cl. .................. 96/29 D; 96/3; 96/55; 96/56.6; 96/66 R; 96/66 HD; 96/74; 96/77; 96/100 R
[58] Field of Search ............ 96/3, 29 D, 77, 55, 96/66.3, 95, 74, 100, 66 R, 56.6, 97, 66 HD

[56] References Cited

U.S. PATENT DOCUMENTS

| | | | |
|---|---|---|---|
| 2,163,166 | 6/1939 | Wilmanns et al. | 96/66 R |
| 2,196,739 | 4/1940 | Peterson | 96/66 R |
| 2,322,027 | 6/1943 | Jelley et al. | 96/97 |
| 2,522,802 | 9/1950 | Sargent et al. | 96/56.6 |
| 2,603,656 | 7/1952 | Martin | 96/66 R |
| 2,603,659 | 7/1952 | Raasch | 96/66 R |
| 2,716,132 | 8/1955 | Martin | 96/66 R |
| 2,728,669 | 12/1955 | Tulagin | 96/56.6 |
| 2,949,360 | 8/1960 | Julian | 96/97 |
| 3,271,152 | 9/1966 | Hanson | 96/97 |
| 3,359,104 | 12/1967 | Viro | 96/3 |
| 3,535,113 | 10/1970 | Hove et al. | 96/56.5 |
| 3,676,124 | 7/1972 | Ohkubo et al. | 96/77 |
| 3,705,035 | 12/1972 | Vetter et al. | 96/3 |
| 3,728,116 | 4/1973 | Waxman et al. | 96/3 |
| 3,746,544 | 7/1973 | Heilmann | 96/66 R |
| 3,779,756 | 12/1973 | Farran et al. | 96/77 |
| 3,839,035 | 10/1974 | Janssens et al. | 96/29 D |

Primary Examiner—David Klein
Assistant Examiner—Richard L. Schilling
Attorney, Agent, or Firm—Walter C. Kehm; Edward G. Comrie

[57] ABSTRACT

A diffusion transfer photographic element containing a lipophilic, non-diffusing color former in a silver halide emulsion layer, or in a layer adjacent thereto, is developed by using a water- and alkali-soluble color developer capable of coupling with the color former to form a diffusible coupled product, the color developer being coated with the silver halide emulsion layer or in any layer of the photographic element or being in an alkaline developing solution.

19 Claims, 1 Drawing Figure

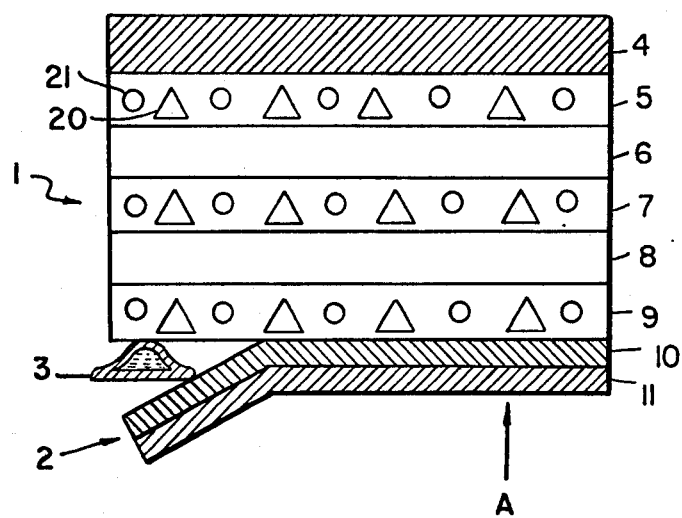

COLOR DEVELOPER FOR DIFFUSION TRANSFER

The present invention relates to new paraphenylenediamine derivatives which are useful as photographic developers, and more particularly as developers for use in diffusion transfer processes.

Paraphenylenediamine and its derivatives are used in photography, particularly as color developers, but these developers have only limited solubility in alkaline solution. Furthermore, paraphenylenediamine developers have only been used in solution, such as in a pod containing alkaline processing solution used in diffusion transfer photography or in an alkaline processing solution applied externally to a film.

Efforts have been made to incorporate the paraphenylenediamine developer within the film itself, but these attempts have not been successful primarily due to the lack of stability of the paraphenylenediamine to aerial oxidation and other forms of environmental degradation. In addition, the incorporated paraphenylenediamine developer tends to fog a silver halide emulsion. Despite the need for a paraphenylenediamine developer that can be incorporated into a photographic film, there has nevertheless been no commercial product marketed employing an incorporated paraphenylenediamine developer.

It is an object of the present invention to provide a derivative of paraphenylenediamine that may be incorporated into a photographic film.

It is another object to provide a paraphenylenediamine derivative that has enchanced water- and alkali-solubility.

It is another object of the present invention to provide such a derivative that has the required stability to resist environmental degradation without sacrificing reactivity of the derivative as a photographic developer.

It is another object of the invention to provide a paraphenylenediamine derivative that may be used as a photographic developer and may be incorporated into a photographic film without danger of fogging the silver halide emulsion.

These and other objects of the invention are provided by the present invention, which resides in a derivative of paraphenylenediamine having a primary amino group available for coupling, and a carboxy or sulfoxy moiety bound to the benzene ring or to a group on a nitrogen atom to provide the developer with the required stability to enable the developer to be incorporated into the film and to solubilize the product obtained from oxidative coupling between a lipophilic coupler and oxidized developer.

The present invention also provides a photographic element comprising a support and a silver halide photographic emulsion and the developer of the present invention carried by said support.

The compounds of the present invention, which are useful as incorporated photographic developers, are represented by the general formula:

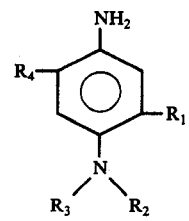

where
$R_1$ is H, COOM or $SO_3M$,
M is H or a cation,
$R_2$ and $R_3$ are independently H, lower alkyl or lower alkanoyl, unsubstituted or substituted by COOM or $SO_3M$, or $R_2$ and $R_3$ taken together represent the atoms necessary to form a saturated heterocyclic ring with the nitrogen atom to which they are attached, and
$R_4$ is hydrogen, lower alkyl or lower alkoxy.

As used herein, the term cation denotes an alkali metal, preferably sodium or potassium, or ammonium cation.

The term lower alkyl denotes a univalent saturated straight or branched hydrocarbon chain containing from 1 to 6 carbon atoms. Representative of such lower alkyl groups are thus methyl, ethyl, propyl, isopropyl, butyl, isobutyl, sec. butyl, tert. butyl, pentyl, isopentyl, neopentyl, tert. pentyl, hexyl, and the like.

The term lower alkoxy denotes a univalent saturated straight or branched hydrocarbon chain containing from 1 to 6 carbon atoms bound to the remainder of the molecule through an ethereal oxygen atom as, for example, methoxy, ethoxy, propoxy, isopropoxy, butoxy, isobutoxy, pentoxy and hexoxy, and the like.

The term lower alkanoyl denotes a univalent straight or branched saturated carbon atom chain containing 1-6 carbon atoms bound to the remainder of the molecule by a carbonyl group as, for example, formyl, propionyl, hexanoyl and the like.

Preferred compounds of the invention are those in which $R_1$ is COOM or $SO_3M$, M is hydrogen, sodium or potassium, $R_2$ and $R_3$ are H, lower alkyl or lower alkanoyl, unsubstituted or substituted by COOM or $SO_3M$ with at least one of $R_2$ and $R_3$ being other than H, or $R_2$ and $R_3$ taken together represent the atoms necessary to form a 3- to 9-membered saturated heterocyclic ring, preferably a 5- to 7-membered ring, said heterocyclic ring having one or two heteroatoms, which may be the same or different, selected from the group consisting of nitrogen, oxygen and sulfur, and $R_4$ is hydrogen, lower alkyl or lower alkoxy.

The compounds of the invention may be prepared by the following synthesis, wherein a 2-halo-5-nitro-benzoic acid or benzene sulfonic acid (II) is reacted with the appropriate amine (III) in a solvent as shown below:

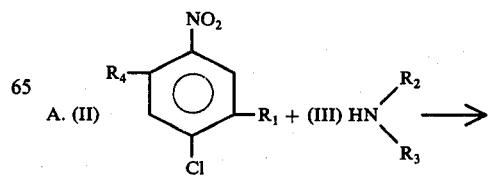

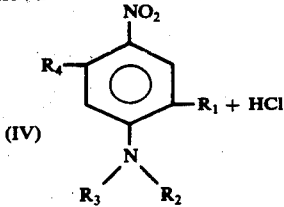

and the nitro group of the intermediate (IV) is reduced using hydrogen and a catalyst, such as platinum, palladium or Raney nickel, to form the final product (I). In the above description, $R_1$, $R_2$, $R_3$ and $R_4$ are as defined above.

Compounds of formula (I) wherein $R_2$ is carboxyalkyl or sulfoxyalkyl may be prepared by the procedure in U.S. Pat. No. 2,163,166.

Salts are readily formed by neutralizing the compound of formula (I), wherein M is hydrogen, with a base MOH, where M is a metal or ammonium cation.

Suitable halonitrobenzoic acids or halonitrobenzene sulfonic acids (II) for use in the synthesis include:

2-nitro-5-chlorobenzoic acid
2-nitro-5-chlorobenzene sulfonic acid
2-nitro-4-methyl-5-chlorobenzoic acid
2-nitro-4-methyl-5-chlorobenzene sulfonic acid
2-nitro-4-hexyl-5-chlorobenzoic acid
2-nitro-4-hexyl-5-chlorobenzene sulfonic acid
2-nitro-4-methoxy-5-chlorobenzoic acid
2-nitro-4-methoxy-5-chlorobenzene sulfonic acid
2-nitro-4-ethoxy-5-chlorobenzoic acid
2-nitro-4-ethoxy-5-chlorobenzene sulfonic acid
2-nitro-4-hexoxy-5-chlorobenzoic acid
2-nitro-4-hexoxy-5-benzene sulfonic acid Suitable amines (III) for use in the synthesis include:

methylamine
methylethylamine
carboxyethylamide
sulfoxyethyl-ethylamine
aziridine
azetidine
pyrrolidine
imidazolidine
pyrazolidine
isoxazolidine
oxazolidine
thiazolidine
isothiazolidine
piperidine
tetrahydro-1,2-, 1,3- or 1,4-thiazine
tetrahydro-1,2-, 1,3- or 1,4-diazine
tetrahydro-1,2- or 1,3-oxazine
morpholine
hexahydro-1,2-, 1,3- or 1,4-azepine
hexahydro-1,2-, 1,3- or 1,4-diazepine
hexahydro-1,2-, 1,3- or 1,4-oxazepine
hexahydro-1,2-, 1,3- or 1,4-thiazepine The compounds of the present invention are hydrophilic, alkali-soluble, diffusible, paraphenylenediamine photographic developers having resistance to aerial oxidation. These developers can be incorporated directly into the photographic film without fogging the silver halide emulsion. Surprisingly, the enhanced stability characteristics of the new developers is not accompanied by a loss of reactivity.

The developers of the invention may be used to advantage in a diffusion transfer photographic process in which a diffusible coupled product is formed as a function of development by reaction between the oxidized developer and a lipophilic color former. In image-wise exposed areas, the oxidized developer will form a diffusible coupled product with the color former because the carboxy and/or sulfoxy group(s) on the developer become incorporated into the coupled product and impart diffusiblity thereto, whereas color former corresponding to unexposed areas will remain non-diffusible and will not be transferred to a receiving sheet. Alternatively, a direct positive silver halide emulsion, such as the internal emulsions or solarizing emulsions discussed in Cole U.S. Pat. No. 3,635,707, can be used so as to form an image-wise distrubution of diffusible coupled product as a function of unexposed areas. Indeed, any diffusion transfer photographic process, such as those in Cole U.S. Pat. No. 3,635,707 and the art in general, may be used so long as there is a coupling between a non-diffusible color former and the developer of the invention whereby the coupled product diffuses, whereas the uncoupled color former does not.

In all of these processes, the developer is preferably coated with the silver halide layer or in any layer of the photographic element, rather than being in the processing solution. The developer is actuated by applying to the film an alkaline processing solution of pH 9 to 14, preferably 10 to 12.5. The developer dissolves in the alkaline solution and reduces exposed silver halide grains, thereby producing oxidized developer that can couple with the lipophilic color former. The processing solution may contain the usual additives, such as preservatives, e.g. $Na_2SO_3$, restainers, e.g. KBr, and the like.

Alternatively, the developer of the invention can be contained in the processing solution itself, which may be part of the film package, as e.g. in a pod in the film package, or can be entirely external of the film package.

There are several advantages in having the developer of the invention incorporated into the film itself, rather than in the processing solution. Thus, there is no decomposition of the developer due to storage thereof in the highly alkaline processing solution. Further, a developer of high reactivity can be used, whereas prior art incorporated developers have sacrificed reactivity for stability in the film. In addition, a uniform distribution of developer can be insured by control over the coating operation. These advantages are possible due to the unique combination of reactivity, resistance to environmental degradation and lack of fogging inherent in the new developer.

However, even where the developer of the invention is used in an alkaline processing solution, its enhanced solubility in alkali will enable high concentrations of developer to be used, thereby resulting in greater reactivity. Further, its increased water-solubility should minimize any allergenic effect.

It will be convenient to use the developer of the invention in the same stoichiometric amounts as known paraphenylenediamine developers, with an excess preferably being used to ensure complete development. In general, there will be an amount of developer of from 30 to 100%, preferably 40 to 80%, based on the weight of the silver halide in the layer associated with the developer. The concentration of developer in a processing solution is suitably 0.2 to 5.0%, preferably 0.4 to 3.0%.

Since the developer of the invention is water-soluble, it is readily incorporated into the silver halide emulsion before the emulsion is coated. Alternatively, the developer can be coated in a separate layer, such as in a gelatin layer.

The lipophilic color formers employed in the invention may be incorporated into the silver halide emulsion layer, or in a layer adjacent thereto, by means of the techniques described in Viro U.S. Pats. Nos. 3,330,772 and 3,359,104, namely by dispersing the lipophilic color former into a high boiling photographically inert oil and mixing the oil dispersion with aqueous gelatin, and then coating this as a separate layer, or combining the mixture with the silver halide emulsion for coating.

A wide variety of lipophilic couplers may be used with the developer of the invention to provide improved diffusion transfer photographic elements. Thus, suitable couplers are those that are a. soluble in high boiling, photographically inert oils;
b. essentially non-diffusible through an aqueous gelatin matrix at pH ranges normally employed in coating operations;
c. essentially non-diffusible through the photographic element at the development pH, e.g. a development pH of 10 to 12.5;
d. reactive with oxidized developer to form a diffusible coupled product to form a dye of desired hue.

The coupler will couple with oxidized developer of the invention in the photographic element to form a diffusible coupled product of desired hue, and due to the sulfoxy and/or carboxy group(s) introduced into the coupled product by the developer moiety, the coupled product is able to diffuse to a receiving element or receiving sheet. The transferred dye image is immobilized in a suitable mordant, such as gelatin, polyvinylpyridine, quaternary ammonium salts, or the like. Suitable image receiving layers or sheets are described, e.g. in U.S. Pat. No. 2,774,668, and other prior art literature.

Color formers meeting the above criteria are well known in the art, e.g. the colorless couplers disclosed in U.S. Pats. Nos. 3,301,772, 3,359,104 and 3,728,116, which are incorporated herein by reference thereto, may be used to advantage. These color formers are of medium molecular weight and become diffusible at a pH of about 12.5 to 13.0. Consequently, the alkaline processing solution must be used at a pH below this, say between pH 10 and 11.5, whether the developer of the invention is in the photographic element or the processing solution, so as to ensure that the color former remains non-diffusible during development and only the coupled product diffuses during development. Preferred color formers are color formers A, B and C below, which are described in U.S. Pat. No. 3,728,116:

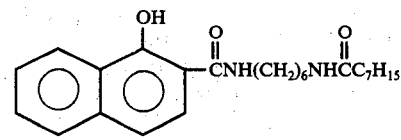

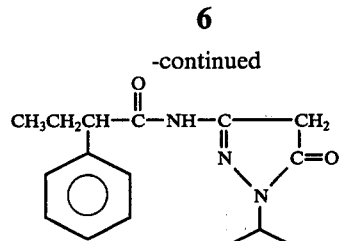

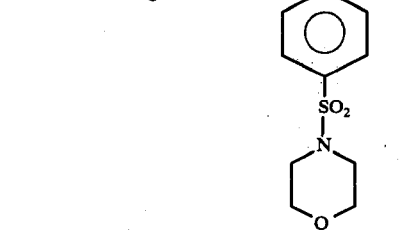

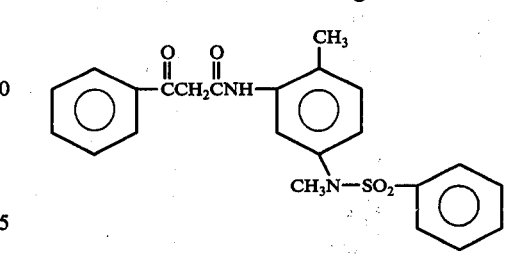

The present invention is illustrated by the following Examples. All parts and proportions as referred to herein and in the appended claims are by weight unless otherwise noted.

EXAMPLE I

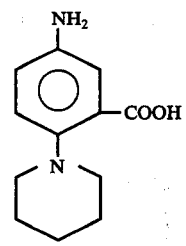

5-amino-2-piperidinobenzoic acid

30 Grams 2-chloro-5-nitrobenzoic acid was added in portions to 150 ml piperidine. The temperature of the reaction was allowed to rise during the addition. After the addition was complete, the reaction was heated at reflux temperature for two hours. The hot reaction mixture was poured into ice water, made acid by the addition of concentrated HCl until precipitation of the product was complete and filtered. The filter cake was recrystallized from ethanol to give 30.4 grams 5-nitro-2-piperidinobenzoic acid. m.p. = 201°–203° C. The nitro compound was reduced catalytically in ethanol with 5% palladium on carbon catalyst to give 5-amino-2-piperidinobenzoic acid. m.p. = 232°–235° C.

| | Analysis | |
|---|---|---|
| | Calculated | Found |
| | C - 65.43 | C - 65.74; 65.61 |
| | H - 7.32 | H - 7.15; 7.17 |
| | N - 12.72 | N - 12.62; 12.84 |

EXAMPLE II

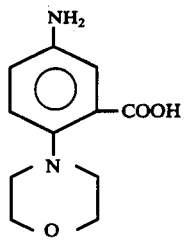

5-amino-2-morpholinobenzoic acid 20.1 Grams 2-chloro-5-nitrobenzoic acid was added in portions to 87 ml morpholine. The temperature of the thick mixture rose to 75° C. After being stirred at reflux temperature for five hours, the mixture was poured into ice water, made acidic with concentrated HCl, filtered, dried and recrystallized from ethanol to give 20.3 grams 2-morpholino-5-nitrobenzoic acid. m.p. = 168°–170° C. The nitro compound was reduced catalytically in ethanol-water (3:1) with 5% palladium on carbon catalyst to give 5-amino-2-morpholinobenzoic acid. m.p. = 307°–308° C.

| Analysis | |
|---|---|
| Calculated | Found |
| C - 59.45 | C - 59.84; 59.58 |
| H - 6.35 | H - 6.34; 6.20 |
| N - 12.61 | N - 12.75; 12.82 |

EXAMPLE III

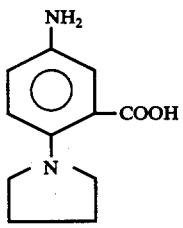

5-amino-2-pyrrolidinobenzoic acid 20.1 Grams 2-chloro-5-nitrobenzoic acid was added in portions to 100 ml pyrrolidine. A cooling bath was applied as necessary during the addition. After the addition was complete, the reaction was heated on a steam bath for three hours, cooled, poured into ice water and made acidic with concentrated HCl until precipitation of product was complete. Recrystallization from ethanol gave 19.4 grams 5-nitro-2-(1-pyrrolidinyl)benzoic acid. m.p. = 224°–266° C dec. The nitro compound was reduced catalytically in ethanol with 5% palladium on carbon catalyst to give 5-amino-2-(1-pyrrolidinyl)benzoic acid. m.p. = 205°–208° C dec.

| Analysis | |
|---|---|
| Calculated | Found |
| C - 64.07 | C - 64.38; 64.33 |
| H - 6.79 | H - 6.65; 6.62 |
| N - 13.59 | N - 13.42; 13.34 |

EXAMPLE IV

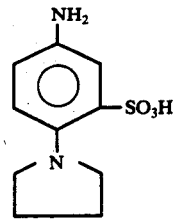

5-amino-2-pyrrolidinobenzenesulfonic acid 72.4 Grams 2-chloro-5-nitrobenzenesulfonic acid was added in portions to 134 ml pyrrolidine, while keeping the temperature below 65° C. After the addition, the reaction was heated at reflux temperature with stirring for 7 hours and allowed to stand overnight at room temperature. The reaction was poured into 800 ml ice water and the solution made strongly acidic with concentrated HCl until light yellow crystals separated. The product was filtered, washed with a little dilute HCl and the moist cake was recrystallized from about 800 ml water to give 70.7 grams 5-nitro-2-pyrrolidinylbenzenesulfonic acid. m.p. = 178°–179° C. The nitro compound was reduced catalytically in ethanol with 5% palladium on carbon catalyst to give 5-amino-2-pyrrolidinyl-benzenesulfonic acid. m.p. = 255°–256° C.

| Analysis | |
|---|---|
| Calculated | Found |
| C - 49.59 | C - 49.57; 49.47 |
| H - 5.79 | H - 5.84; 5.86 |
| N - 11.57 | N - 10.84; 10.83 |

EXAMPLE V

A photographic element is made by coating on a polyester film base a mixture of 100 g of bromoiodide emulsion containing 5% silver sensitized to red light and 50 g of color former dispersion containing 4 g of color former "A" and 8 cc of dibutylphthalate in 6% gelatin solution. The mixture is coated with the aid of coating aid and hardener to 0.6 g silver/meter². Two strips of this coating are exposed imagewise. One strip is contacted with a 10 micron thick acid-treated gelatin receiving sheet in a developer solution with the following composition:

| Solution A | |
|---|---|
| Sodium sulfite | 8 grams |
| Sodium hexametaphosphate | 1 gram |
| 5-amino-2-morpholinobenzoic acid | 5 grams |
| Sodium carbonate, monohydrate | 10 grams |
| Sodium bromide | 1 gram |
| Water to make | 1 liter |

After 2 minutes contact in the solution the negative material is peeled apart from the receiving sheet, which now exhibits a transferred cyan colored negative image.

The second strip is contacted with a receiving sheet in a developer solution (Solution B) in which 5-amino-2-morpholinobenzoic acid of Solution A is replaced by N-ethyl-N-β-hydroxyethylp-phenylene diamine. After two minutes contact, the negative material is peeled apart from the receiving sheet which shows no evidence of cyan dye transfer.

EXAMPLE VI

Example V was repeated except that color former "B" was used, and silver halide emulsion was sensitized to green light. After 2 minutes contact in Solution A, the receiving element showed a magenta negative image when contacted in the developer. No magenta dye was transferred when developer Solution B was used.

EXAMPLE VII

Example V was repeated except that color former "C" was used and the silver halide emulsion layer was unsensitized. A yellow colored negative image was transferred to the receiving sheet when developed with Solution A, whereas no dye transfer was observed with Solution B.

EXAMPLE VIII

The photographic element prepared in Example V was first coated over with 3% gelatin solution to a gelatin layer thickness of 1.6 microns and then with the green sensitive emulsion containing color former B described in Example VI. After three minutes contact in Solution A, a negative two-color image was observed in the receiving element.

EXAMPLE IX

Following the procedure of Example VIII, a photographic element consisting of a red sensitive silver halide layer containing color former "A", a gelatin separation layer and a green sensitive silver halide layer containing color former "B" on a polyester film base was prepared, except that the 3% gelatin solution used for the separation layers also contains 2% 5-amino-2-morpholinobenzoic acid. The coated strip is contacted with a receiving sheet in a processing solution containing:

| | | |
|---|---|---|
| Sodium sulfite | 8 | grams |
| Sodium hexametaphosphate | 1 | gram |
| Sodium carbonate, monohydrate | 10 | grams |
| Sodium bromide | 1 | gram |
| Water to make | 1 | liter |

After 3 minutes contact the receiving sheet was peeled apart and revealed a two color negative image transfer.

EXAMPLE X

A photosenstive element comprised of the following layers is coated:

1. Polyester film base;
2. Color former "A" dispersed in dibutylphthalate oil in a gelatin matrix containing Carey-Lea yellow colloidal silver. The coating weight of the color former is 0.5 g/m²;
3. A very thin (0.5 microns) layer of gelatin containing 2.5-ditertiary amyl hydroguinone as an anatioxidant;
4. A bromoiodide unsensitized silver halide emulsion containing a non-diffusing coupler, 1-(2,4,6-trichlorophenyl)-3-{3-[(2,4-ditertiaryamylphenoxy)-acetamido]-benzamido}-5-oxo-2-pyrazoline.

The silver halide emulsion is coated to a weight of 1.0 g Ag/m² color former coverage.

The photosensitive element is exposed imagewise and then married to a receiving sheet in a developer with the following composition:

| | | |
|---|---|---|
| 5-amino-2-morpholinobenzoic acid | 5.0 | grams |
| Phenidone B | 0.125 | grams |
| Metol | 0.125 | grams |
| Sodium thiosulfate | 1.0 | grams |
| Sodium sulfite | 4.0 | grams |
| Benzyl alcohol | 4.0 | ml. |
| Potassium hydroxide | 21.0 | grams |
| Boric Acid | 18.0 | grams |
| Hydroxylamine sulfate | 2.0 | grams |
| Nitrilotriacetic acid, sodium salt | 4.0 | grams |
| Sodium chloride | 2.5 | grams |
| Alipal CO-436* | 0.83 | ml. |
| Methocel** | 1.0 | grams |
| Water to make | 1 | liter |

*Trade name for the ammonia salt of a sulfonated nonyl phenoxy poly(alkyleneoxy) ethanol sold by the GAF Corp.
**Methyl cellulose supplied by Dow Chem. Co.

After 3 minutes the receiving sheet is peeled off containing a cyan positive image.

EXAMPLE XI

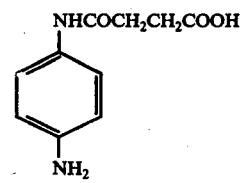

p-Nitrosuccinanilic acid, prepared according to J. Am. Chem. Soc., 67, 1220 was reduced catalytically in ethanol with 5% palladium on carbon catalyst to give p-aminosuccinanilic acid. m.p. = 180°–181° C.

EXAMPLE XII

4-Amino-N-ethyl-3-methyl-N-(β-sulfoethyl)aniline was prepared according to the method described in J. Am. Chem. Soc., 78, 5827.

EXAMPLE XIII

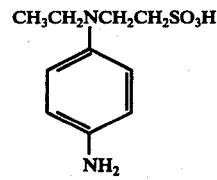

N-Ethyl-N-(2-sulfoethyl)aniline prepared and nitrosated according to the method described in J. Am. Chem. Soc., 78, 5827 for the preceding analogous compound and was reduced catalytically to give 4-amino-N-ethyl-N-(β-sulfoethyl)aniline.

| Calculated | Found |
|---|---|
| C - 49.18 | C - 48.53; 48.93 |
| H - 6.55 | H - 6.64; 6.72 |
| N - 11.48 | N - 11.06; 10.87 |
| S - 13.11 | S - 13.33; 13.12 |

EXAMPLE XIV

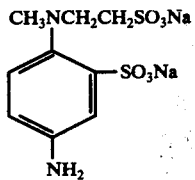

N-Methyl-N-(4-Nitro-2-sulfophenyl)taurine was prepared as described in Bios Report 986. The nitro compound was reduced catalytically in ethanol-water (2:1) with 5% palladium on carbon catalyst to give N-(4-amino-2-sulfophenyl)-N-methyltaurine.

|  | Calculated | Found |
|---|---|---|
|  | C - 27.69 | C - 27.64; 29.18 |
|  | H - 4.10 | H - 4.01; 4.05 |
|  | N - 7.18 | N - 7.30; 7.29 |
|  | S - 16.41 | S - 16.40; 16.65 |
|  | Na - 11.79 | Na - 12.04; 11.78 |

The drawing illustrates a film unit useful in carrying out the present invention.

The drawing shows a film unit 1, receiving sheet 2 and rupturable pod 3. The film unit 1 is exposed to actinic radiation in the direction shown by arrow A and, after exposure, the film unit 1 is married to receiving sheet 2 and the film unit 1, pod 3 and receiving sheet 2 are passed through compression rollers (not shown) in a conventional manner to rupture the contents of the pod 3. Pod 3 contains an alkaline processing solution of a pH at which the color former in the film unit is not diffusible.

The film unit 1 has a support 4, such as a polyester film base, on which is coated the following layers:

5 — as direct positive red-sensitive silver halide emulsion, a developer of the invention, and a color former dispersed in an oily material;
6 — gelatin separation layer;
7 — a direct positive green-sensitive silver halide emulsion, a developer of the invention, and a color former dispersed in an oily material;
8 — gelatin separation layer containing colloidal yellow silver;
9 — a direct positive blue-sensitive silver halide emulsion, a developer of the invention, and a color former dispersed in an oily material;
10 — image receiving layer
11 — white opaque film or paper base.

The silver halide grains 20 and the oily material 21 containing the color former are shown schematically in layers 5, 7 and 9. The developer is incorporated in layers 5 through 9; the image-receiving layer is a dyeable material as described above and needs no further treatment to obtain a positive image corresponding to unexposed areas of the film unit; the receiving sheet 2 is simply peeled from the film unit 1 and the image is viewed by looking at layer 10.

It is to be understood that the developer can be in the pod 3 rather than in the emulsion layers.

Other film packages may be employed including, without limitation, those described in Cole U.S. Pat. No. 3,635,707.

In the description and Examples above, gelatin was used as a hydrophilic colloidal matrix. It is understood, however, that gelatin substitutes, such as polyvinyl alcohol, methyl cellulose, casein and other hydrophilic colloids, may also be employed.

What we claim is:

1. A process of producing a photographic image in a diffusion transfer photographic element, said photographic element comprising at least one supported light sensitive silver halide emulsion layer and a dispersion of a lipophilic color former in a high boiling photographically inert oil incorporated into, or in a layer adjacent, each said silver halide emulsion layer, which comprises developing said photographic element, after image-wise exposure to actinic radiation, in an alkaline medium of a pH below 12.5 in the presence of a color developer capable of developing silver halide and having the general formula:

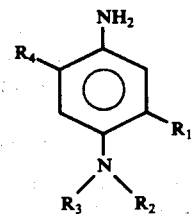

where
$R_1$ is COOM or $SO_3M$,
M is H or a cation,
$R_2$ and $R_3$ are H, lower alkyl or lower alkanoyl, unsubstituted or substituted by COOM or $SO_3M$, with at least one of $R_2$ and $R_3$ being other than H, or $R_2$ and $R_3$ taken together represent the atoms necessary to form a saturated heterocyclic ring with the nitrogen atom to which they are attached, and $R_4$ is hydrogen, lower alkyl or lower alkoxy, said lipophilic color former being fast to diffusion at said pH and being reactive with oxidized color developer formed during development to form a coupled product that is diffusible at said pH, and allowing the coupled product to diffuse to an image receiving means for immobilizing said coupled product.

2. The process according to claim 1, wherein said color developer is present in each said silver halide emulsion layer or in any other layer of said photographic element.

3. The process according to claim 1, wherein said color developer is in said alkaline medium.

4. The process according to claim 1, wherein said silver halide emulsion layers are direct positive silver halide emulsion layers.

5. The process according to claim 4, wherein there are a plurality of said silver halide emulsion layers, each sensitized to light of a different color, and the color former associated with each silver halide emulsion layer is reactive to form a coupled product complementary in color to the color of the light to which its associated silver halide layer is sensitized.

6. The process according to claim 1, wherein $R_2$ and $R_3$ when taken together represent the atoms necessary to form a 3- to 9-membered saturated heterocyclic ring, said heterocyclic ring having one or two heteroatoms, which may be the same or different, selected from the group consisting of nitrogen, oxygen and sulfur.

7. The process according to claim 6, wherein said heterocyclic ring has 5 to 7 ring members.

8. The process according to claim 1, wherein the color developer is

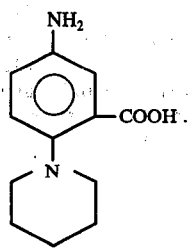

9. The process according to claim 1, wherein the color developer is

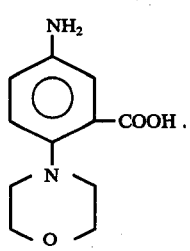

10. The process according to claim 1, wherein the color developer is

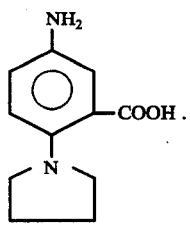

11. The process according to claim 1, wherein the color developer is

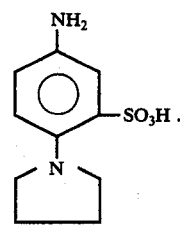

12. A photographic element, which comprises at least one supported light sensitive silver halide emulsion layer, a dispersion of a lipophilic color former in a high boiling photographically inert oil incorporated into, or in a layer adjacent to, each said silver halide emulsion layer, and a color developer in said silver halide emulsion layer or in any other layer of said photographic element, said color developer capable of developing silver halide and having the formula:

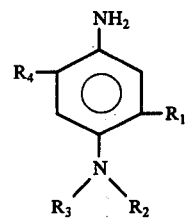

where
$R_1$ is COOM or $SO_3M$,
M is H or a cation,
$R_2$ and $R_3$ are H, lower alkyl or lower alkanoyl, unsubstituted or substituted by COOM or $SO_3M$, with at least one of $R_2$ and $R_3$ being other than H, or $R_2$ and $R_3$ taken together represent the atoms necessary to form a saturated heterocyclic ring with the nitrogen atom to which they are attached, and
$R_4$ is hydrogen, lower alkyl or lower alkoxy, lipophilic color former being fast to diffusion at a pH below 12.5 at which the photographic element is developed and being reactive with oxidized color developer former during development to form a coupled product that is diffusible at the development pH, and an image receiving means for immobilizing coupled product transferred thereto.

13. The photographic element according to claim 12, wherein $R_2$ and $R_3$ when taken together represent the atoms necessary to form a 3- to 9-membered saturated heterocyclic ring, said heterocyclic ring having one or two heteroatoms, which may be the same or different, selected from the group consisting or nitrogen oxygen and sulfur.

14. The photographic element according to claim 12 wherein said heterocyclic ring has 5 to 7 ring members.

15. The photographic element according to claim 12, wherein the color developer is

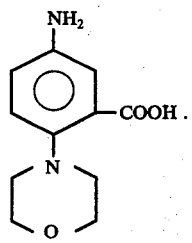

16. The photographic element according to claim 12, wherein the color developer is

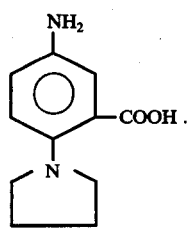

17. The photographic element according to claim 12, wherein the color developer is

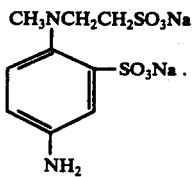

18. The photographic element according to claim 12, wherein said silver halide emulsion layers are direct positive silver halide emulsion layers.

19. The photographic element according to claim 18, wherein there are a plurality of said silver halide emulsion layers, each sensitized to light of a different color, and the color former associated with each silver halide emulsion layer is reactive to form a coupled product complementary in color to the color of the light to which its associated silver halide layer is sensitized.

* * * * *